United States Patent
Salo et al.

(10) Patent No.: US 9,002,452 B2
(45) Date of Patent: Apr. 7, 2015

(54) ELECTRICAL THERAPY FOR DIASTOLIC DYSFUNCTION

(75) Inventors: Rodney W. Salo, Fridley, MN (US); Matthew Salo, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1708 days.

(21) Appl. No.: 10/703,398

(22) Filed: Nov. 7, 2003

(65) Prior Publication Data

US 2005/0102002 A1    May 12, 2005

(51) Int. Cl.
*A61N 1/365* (2006.01)
*A61N 1/362* (2006.01)

(52) U.S. Cl.
CPC ........... *A61N 1/3627* (2013.01); *A61N 1/36514* (2013.01)

(58) Field of Classification Search
USPC ..................................... 607/17, 18, 23, 24, 9
See application file for complete search history.

(56) References Cited

U.S. PATENT DOCUMENTS

| | | | |
|---|---|---|---|
| 3,995,623 A | 12/1976 | Blake et al. | |
| 4,354,497 A | 10/1982 | Kahn | |
| 4,401,119 A | 8/1983 | Herpers | |
| 4,432,362 A | 2/1984 | Leckrone et al. | |
| 4,485,813 A | 12/1984 | Anderson et al. | |
| 4,674,518 A | 6/1987 | Salo | |
| 4,686,987 A | 8/1987 | Salo et al. | |
| 4,719,921 A * | 1/1988 | Chirife ............................ | 607/23 |
| 4,872,459 A | 10/1989 | Pless et al. | |
| 4,880,005 A | 11/1989 | Pless et al. | |
| 4,922,907 A | 5/1990 | Hedin et al. | |
| 4,928,688 A | 5/1990 | Mower | |
| 4,945,909 A | 8/1990 | Fearnot et al. | |
| 5,014,698 A | 5/1991 | Cohen | |
| 5,083,563 A | 1/1992 | Collins | |
| 5,129,394 A | 7/1992 | Mehra | |
| 5,156,149 A | 10/1992 | Hudrlik | |
| 5,158,079 A | 10/1992 | Adams et al. | |
| 5,163,429 A * | 11/1992 | Cohen .............................. | 607/4 |
| 5,168,869 A | 12/1992 | Chirife | |
| 5,174,289 A | 12/1992 | Cohen | |

(Continued)

FOREIGN PATENT DOCUMENTS

| | | |
|---|---|---|
| EP | 0474958 A2 | 3/1992 |
| EP | 0970721 A2 | 1/2000 |

(Continued)

OTHER PUBLICATIONS

"International Search Report for corresponding PCT Application No. PCT/US2004/037129", (Mar. 15, 2005), 4 pgs.

(Continued)

*Primary Examiner* — Michael Kahelin
(74) *Attorney, Agent, or Firm* — Schwegman Lundberg & Woessner, P.A.

(57) ABSTRACT

Pacing pulses are delivered to one or more cardiac regions to improve diastolic performance in patients having diastolic dysfunction and/or heart failure. A cardiac pacing system executes a pacing algorithm using a parameter indicative of the diastolic performance as an input. The pacing pulses excite the one or more cardiac regions to redistribute the loading on the ventricular wall during diastole, thereby improving the diastolic performance by lowering the degree of cardiac wall motion dyssynchrony associated with diastolic dysfunction.

14 Claims, 6 Drawing Sheets

(56) References Cited

U.S. PATENT DOCUMENTS

| | | | |
|---|---|---|---|
| 5,179,949 A | 1/1993 | Chirife | |
| 5,188,106 A | 2/1993 | Nappholz et al. | |
| 5,233,985 A | 8/1993 | Hudrlik | |
| 5,267,560 A | 12/1993 | Cohen | |
| 5,271,395 A | 12/1993 | Wahlstrand et al. | |
| 5,318,595 A * | 6/1994 | Ferek-Petric et al. | 607/17 |
| 5,324,326 A | 6/1994 | Lubin | |
| 5,330,511 A | 7/1994 | Boute | |
| 5,334,222 A | 8/1994 | Salo et al. | |
| 5,368,040 A | 11/1994 | Carney | |
| 5,370,665 A | 12/1994 | Hudrlik | |
| 5,372,607 A | 12/1994 | Stone et al. | |
| 5,417,717 A | 5/1995 | Salo et al. | |
| 5,433,205 A | 7/1995 | Visveshwara | |
| 5,464,434 A | 11/1995 | Alt | |
| 5,514,161 A | 5/1996 | Limousin | |
| 5,514,163 A | 5/1996 | Markowitz et al. | |
| 5,515,849 A | 5/1996 | Murashita et al. | |
| 5,527,347 A | 6/1996 | Shelton et al. | |
| 5,534,016 A | 7/1996 | Boute | |
| 5,549,650 A | 8/1996 | Bornzin et al. | |
| 5,554,177 A | 9/1996 | Kieval et al. | |
| 5,584,867 A | 12/1996 | Limousin et al. | |
| 5,584,868 A * | 12/1996 | Salo et al. | 607/17 |
| 5,609,612 A | 3/1997 | Plicchi et al. | |
| 5,626,620 A | 5/1997 | Kieval et al. | |
| 5,626,623 A | 5/1997 | Kieval et al. | |
| 5,628,777 A | 5/1997 | Moberg et al. | |
| 5,674,259 A | 10/1997 | Gray | |
| 5,683,429 A | 11/1997 | Mehra | |
| 5,690,689 A | 11/1997 | Sholder | |
| 5,700,283 A | 12/1997 | Salo | |
| 5,713,930 A | 2/1998 | van der Veen et al. | |
| 5,716,383 A | 2/1998 | Kieval et al. | |
| 5,728,140 A | 3/1998 | Salo et al. | |
| 5,749,906 A | 5/1998 | Kieval et al. | |
| 5,755,766 A | 5/1998 | Chastain et al. | |
| 5,797,970 A | 8/1998 | Pouvreau | |
| 5,800,471 A | 9/1998 | Baumann | |
| 5,824,019 A | 10/1998 | Rueter et al. | |
| 5,935,160 A | 8/1999 | Auricchio et al. | |
| 6,038,483 A | 3/2000 | KenKnight et al. | |
| 6,044,298 A | 3/2000 | Salo et al. | |
| 6,058,329 A | 5/2000 | Salo et al. | |
| 6,108,577 A | 8/2000 | Benser | |
| 6,112,117 A | 8/2000 | KenKnight et al. | |
| 6,128,534 A | 10/2000 | Park et al. | |
| 6,136,021 A | 10/2000 | Tockman et al. | |
| 6,144,880 A | 11/2000 | Ding et al. | |
| 6,151,524 A | 11/2000 | Krig et al. | |
| 6,152,955 A | 11/2000 | KenKnight et al. | |
| 6,198,952 B1 | 3/2001 | Miesel | |
| 6,208,901 B1 | 3/2001 | Hartung | |
| 6,223,082 B1 | 4/2001 | Bakels et al. | |
| 6,273,856 B1 | 8/2001 | Sun et al. | |
| 6,280,389 B1 | 8/2001 | Ding et al. | |
| 6,309,350 B1 | 10/2001 | VanTassel et al. | |
| 6,311,089 B1 | 10/2001 | Mann et al. | |
| 6,314,322 B1 * | 11/2001 | Rosenberg | 607/17 |
| 6,351,673 B1 | 2/2002 | Ding et al. | |
| 6,360,127 B1 | 3/2002 | Ding et al. | |
| 6,398,738 B1 | 6/2002 | Millar | |
| 6,411,848 B2 | 6/2002 | Kramer et al. | |
| 6,418,346 B1 * | 7/2002 | Nelson et al. | 607/59 |
| 6,430,439 B1 | 8/2002 | Wentkowski et al. | |
| 6,438,421 B1 | 8/2002 | Stahmann et al. | |
| 6,449,510 B1 | 9/2002 | Albers et al. | |
| 6,480,742 B2 | 11/2002 | Stahmann et al. | |
| 6,507,756 B1 | 1/2003 | Heynen et al. | |
| 6,512,952 B2 | 1/2003 | Stahmann et al. | |
| 6,522,921 B2 | 2/2003 | Stahmann et al. | |
| 6,522,923 B1 | 2/2003 | Turcott | |
| 6,542,775 B2 | 4/2003 | Ding et al. | |
| 6,553,258 B2 | 4/2003 | Stahmann et al. | |
| 6,597,951 B2 | 7/2003 | Kramer et al. | |
| 6,628,988 B2 | 9/2003 | Kramer et al. | |
| 6,654,637 B2 | 11/2003 | Rouw et al. | |
| 6,666,826 B2 | 12/2003 | Salo et al. | |
| 6,684,103 B2 | 1/2004 | Ding et al. | |
| 6,754,532 B1 * | 6/2004 | Ferek-Petric | 607/17 |
| 6,795,732 B2 * | 9/2004 | Stadler et al. | 607/17 |
| 6,810,284 B1 | 10/2004 | Bradley | |
| 6,832,113 B2 | 12/2004 | Belalcazar | |
| 6,839,593 B1 | 1/2005 | Sun et al. | |
| 6,856,836 B2 | 2/2005 | Ding et al. | |
| 6,859,665 B2 | 2/2005 | Ding et al. | |
| 6,892,095 B2 | 5/2005 | Salo | |
| 6,970,742 B2 * | 11/2005 | Mann et al. | 607/23 |
| 7,024,244 B2 | 4/2006 | Muhlenberg et al. | |
| 7,037,266 B2 | 5/2006 | Ferek-Petric et al. | |
| 7,092,759 B2 * | 8/2006 | Nehls et al. | 607/19 |
| 7,184,835 B2 | 2/2007 | Kramer et al. | |
| 7,529,585 B2 | 5/2009 | Yu et al. | |
| 7,869,871 B2 | 1/2011 | Salo et al. | |
| 2001/0047194 A1 | 11/2001 | Thompson et al. | |
| 2002/0002389 A1 | 1/2002 | Bradley et al. | |
| 2002/0123769 A1 | 9/2002 | Panken et al. | |
| 2002/0151938 A1 | 10/2002 | Corbucci | |
| 2003/0055345 A1 | 3/2003 | Eigler | |
| 2003/0074029 A1 | 4/2003 | Deno et al. | |
| 2003/0078628 A1 * | 4/2003 | Holmstrom et al. | 607/9 |
| 2003/0105496 A1 | 6/2003 | Yu et al. | |
| 2003/0120319 A1 | 6/2003 | Sun et al. | |
| 2003/0130581 A1 | 7/2003 | Salo | |
| 2003/0144702 A1 | 7/2003 | Yu et al. | |
| 2003/0144703 A1 | 7/2003 | Yu et al. | |
| 2004/0015081 A1 | 1/2004 | Kramer et al. | |
| 2004/0019365 A1 | 1/2004 | Ding et al. | |
| 2004/0147966 A1 | 7/2004 | Ding et al. | |
| 2004/0193223 A1 | 9/2004 | Kramer et al. | |
| 2005/0038477 A1 | 2/2005 | Kramer et al. | |
| 2005/0115561 A1 | 6/2005 | Stahmann et al. | |
| 2006/0089679 A1 | 4/2006 | Zhu et al. | |
| 2007/0239219 A1 | 10/2007 | Salo et al. | |
| 2009/0198299 A1 | 8/2009 | Yu et al. | |

FOREIGN PATENT DOCUMENTS

| | | |
|---|---|---|
| WO | WO-99/10042 A1 | 3/1999 |
| WO | WO-99/58191 A1 | 11/1999 |
| WO | WO-01/76689 A2 | 10/2001 |
| WO | WO-02/087694 A1 | 11/2002 |
| WO | WO-02087693 A2 | 11/2002 |
| WO | WO-03041797 A2 | 5/2003 |
| WO | WO-2004/011088 A1 | 2/2004 |
| WO | WO-2004/069333 A2 | 8/2004 |
| WO | WO-2005/046788 A2 | 5/2005 |

OTHER PUBLICATIONS

Auricchio, A., "Effect of Pacing Chamber and Atrioventricular Delay on Acute Systolic Function of Paced Patients With Congestive Heart Failure. The Pacing Therapies for Congestive Heart Failure Study Group. The Guidant Congestive Heart Failure Research Group", *Circulation*, 99(23), (1999), 2993-3001.

Auricchio, A , "The Pacing Therapies for Congestive Heart Failure (PATH-CHF) Study: Rationale, Design, and Endpoints of a Prospective Radomized Multicenter Study", *The American Journal of Cardiology*, 83(5B), (1999), 130D-135D.

Breithardt, O. A., "Acute Effects of Cardiac Resynchronization Therapy on Left Ventricular Doppler Indices in Patients With Congestive Heart Failure", *American Heart Journal*, 143(1), (2002), 34-44.

Breithardt, O. A., "Echocardiographic Quantification of Left Ventricular Asynchrony Predicts an Acute Hemodynamic Benefit of Cardiac Resynchronization Therapy", *Journal of the American College of Cardiology*, 40(3), (2002), 536-545.

Butter, C., "Effect of Resynchronization Therapy Stimulation Site on the Systolic Function of Heart Failure Patients", *Circulation*, 104(25), (Dec. 18, 2001), 3026-3029.

(56) References Cited

OTHER PUBLICATIONS

Chen, H. H., et al., "Diastolic Heart Failure in the Community: Clinical Profile, Natural History, Therapy, and Impact of Proposed Diagnostic Criteria", *Journal of Cardiac Failure*, 8(5), (2002), 279-287.

Curtis, J. P., et al., "The Association of Left Ventricular Ejection Fraction Mortality, and Cause of Death in Stable Outpatients With Heart Failure", *Journal of the American College of Cardiology*, 42(4), (2003),736-742.

Ding, J., et al., "Cardiac Pacing Using Adjustable Atrio-Ventricular Delays", U.S. Appl. No. 11/049,181, filed Feb. 2, 2005, 35 pgs.

Kass, D. A., "Improved Left Ventricular Mechanics From Acute VDD Pacing in Patients With Dilated Cardiomyopathy and Ventricular Conduction Delay", *Circulation*, 99(12), (1999), 1567-1573.

Kawaguchi, M., "Quantitation of Basal Dyssynchrony and Acute Resychronization from Left or Biventricular Pacing by Novel Echo-Contrast Variability Imaging", *Journal of the American College of Cardiology*, 39(12), (2002), 2052-2058.

Kerwin, W. F., "Ventricular Contraction Abnormalities in Dilated Cardiomyopathy: Effect of Biventricular Pacing to Correct Interventricular Dyssynchrony", *Journal of the American College of Cardiology*, 35(5), (2000), 1221-1227.

Kim, H., et al., "Integrated MEMS for Pressure Transponder", *1997 International Conference on Solid State Sensors and Actuators. Transducers '97*, vol. 2., (Chicago, IL),(1997), 1011-1014.

Le Rest, C. "Use of Left Ventricular Pacing in Heart Failure: Evaluation by Gated Blood Pool Imaging", *Journal of Nuclear Cardiology*, 6(6), (Nov./Dec. 1999), 651-656.

Little, W. C., "Clinical Evaluation of Left Ventricular Diastolic Performance", *Progress in Cardiovascular Disease*, 32(4), (1990), 273-290.

Nelson, G. S., "Left Ventricular or Biventricular Pacing Improves Cardiac Function at Diminished Energy Cost in Patients With Dilated Cardiomyopathy and Left Bundle-Branch Block", *Circulation*, 102(25), (2000),3053-3059.

Nelson, G. S., "Predictors of Systolic Augmentation From Left Ventricular Preexcitation in Patients with Dilated Cardiomyopathy and Intraventricular Conduction Delay", *Circulation*, 101, (2000), 2703-2709.

Prinzen, F. W., "Mapping of Regional Myocardial Strain and Work During Ventricular Pacing: Experimental Study Using Magnetic Resonance Imaging Tagging", *Journal of the American College of Cardiology*, 33(6), (1999), 1735-1742.

Redfield, M. M., et al., "Burden of Systolic and Diastolic Ventricular Dysfunction in the Community", *JAMA*, 289(2), (2003),194-202.

Ritter, P. , et al., "A Built-In System Based on the Peak Endocardial Acceleration (PEA) for AV-Delay Optimization in DDDR Pacing", *PACE*, 20(5) (Part II), (Abstract of Paper presented at EUROPACE '97), (May 1997), 1567.

Søgaard, Peter , "Impact of Acute Biventricular Pacing on Left Ventricular Performance and Volumes in Patients with Severe Heart Failure: a tissue Doppler and three-dimensional echocardiographic study", *Cardiology*, 95, (2001), 173-182.

Stellbrink, C., "Impact of Cardiac Resynchronization Therapy Using Hemodynamically Optimized Pacing on Left Ventricular Remodeling in Patients With Congestive Heart Failure and Ventricular Conduction Disturbances", *Journal of the American College of Cardiology*, vol. 38, No. 7, (Dec. 2001), 1957-1965.

Watanabe, M., et al., "Developmental Remodeling and Shortening of Cardiac Outflow Tract Involves Myocyte Programmed Cell Death", *Development*, 125 (19), (1998),3809-3820.

Xiao, H. B., "Differing effects of right ventricular pacing and left bundle branch on left ventricular function", *British Heart Journal*, 69(2), (1993), 166-173.

Yu, C.-M., et al., "High Prevalence of Left Ventricular Systolic and Diastolic Asynchrony in Patients With Congestive Heart Failure and Normal QRS Duration", *Heart*, 89, (2003), 54-60.

Yu, C.-M., "Tissue Doppler Echocardiographic Evidence of Reverse Remodeling and Improved Synchronicity by Simultaneously Delaying Regional Contraction After Biventricular Pacing Therapy in Heart Failure", *Circulation*, 105, (2002), 438-445.

Zile, M.D., M. R., et al., "Diastolic Heart Failure: Diagnosis and Treatment", *Clinical Cornerstone*, 3(2), http://cardiology.medscape.com/ExcerptaMed/ClinCornerstne/200.../pnt-clc0302.03.zile.htm, ((Observed Jul. 16, 2001)), 14 pgs.

U.S. Appl. No. 11/278,330 Non-Final Office Action mailed Dec. 24, 2008, 32 pgs.

U.S. Appl. No. 11/278,330 Response filed Mar. 24, 2009 to Non Final Office Action mailed Dec. 24, 2008, 13 pgs.

U.S. Appl. No. 11/278,330 Non Final Office Action Mailed Oct. 16, 2009, 13 pgs.

U.S. Appl. No. 11/278,330 ,Final Office Action mailed May 22, 2009, 13 pgs.

U.S. Appl. No. 11/278,330, Response filed Aug. 24, 2009 to Final Office Action mailed May 22, 2009, 10 pgs.

"International Application Serial No. PCT/US2004/037129, Written Opinion mailed Mar. 15, 2005", 6 pgs.

"European Application Serial No. - 07759851.4 , Office Action mailed Jun. 22, 2009", 2 pgs.

U.S. Appl. No. 11/567,933, Non Final Office Action mailed Nov. 17, 2010, 6 pgs.

U.S. Appl. No. 12/424,136, Non Final Office Action mailed Nov. 19, 2010, 7 pgs.

"European Application Serial No. 07759851.4, Response filed Dec. 30, 2009 to Office Actlon mailed Jun. 22, 2009", 10 pgs.

"Japanese Application Serial No. 2006-539696, Final Office Action mailed Oct. 25, 2010", 2 pgs.

"Application Serial No. 04800869.2, Communication dated Feb. 12, 2009", 5 pgs.

"Application No. 04800869.2, Response filed Jun. 17, 2009 to Communication dated Feb. 12, 2009", 16 pgs.

"Japnese Application Serial No. 2006-539696, Office Action mailed Apr. 7, 2010", (w/ English Translation), 5 pgs.

"Japnese Application Serial No. 2006-539696, Response filed Jul. 2, 2010 to Office Action Apr. 7, 2010", (w/ English Translation of Amended Claims), 16 pgs.

U.S. Appl. No. 10/314,899 Final Office Action mailed Apr. 24, 2006, 11 pgs.

U.S. Appl. No. 10/314,899 Non Final Office Action mailed Dec. 15, 2005, 17 pgs.

U.S. Appl. No. 10/314,899 Response filed Mar. 15, 2006 to Non Final Office Action mailed Dec. 15, 2005, 11 pgs.

U.S. Appl. No. 10/314,899 Response filed Jun. 23, 2006 to Final Office Action mailed Apr. 24, 2006, 10 pgs.

U.S. Appl. No. 10/314,910 Non Final Office Action mailed Dec. 16, 2005, 19 pgs.

U.S. Appl. No. 10/314,910 Response filed Mar. 16, 2006 to Non Final Office Action mailed Dec. 16, 2005, 14 pgs.

* cited by examiner

ELECTRICAL THERAPY FOR DIASTOLIC DYSFUNCTION

CROSS-REFERENCE TO RELATED APPLICATIONS

This application is related to, commonly assigned U.S. patent application Ser. No. 10/038,936, "METHOD AND APPARATUS FOR MEASURING LEFT VENTRICULAR PRESSURE," filed on Jan. 4, 2002, U.S. patent application Ser. No. 10/314,910, "METHOD AND APPARATUS FOR OPTIMIZING VENTRICULAR SYNCHRONY DURING DDD RESYNCHRONIZATION THERAPY USING ADJUSTABLE ATRIO-VENTRICULAR DELAYS," filed on Dec. 9, 2002, U.S. patent application Ser. No. 10/314,899, "METHOD AND APPARATUS FOR OPTIMIZING STROKE VOLUME DURING DDD RESYNCHRONIZATION THERAPY USING ADJUSTABLE ATRIO-VENTRICULAR DELAYS," filed on Dec. 9, 2002, and U.S. patent application Ser. No. 10/402,324, "METHOD AND APPARATUS FOR QUANTIFICATION OF CARDIAC WALL MOTION ASYNCHRONY," filed on Mar. 28, 2003, all assigned to Cardiac Pacemakers, Inc., which are hereby incorporated by reference.

TECHNICAL FIELD

This document relates generally to cardiac rhythm management and particularly, but not by way of limitation, to a pacing system for improving diastolic performance.

BACKGROUND

The heart is the center of a person's circulatory system. It includes an electro-mechanical system performing two major pumping functions. The heart includes four chambers: right atrium (RA), right ventricle (RV), left atrium (LA), and left ventricle (LV). The left portions of the heart, including LA and LV, draw oxygenated blood from the lungs and pump it to the organs of the body to provide the organs with their metabolic needs for oxygen. The right portions of the heart, including RA and RV, draw deoxygenated blood from the body organs and pump it to the lungs where the blood gets oxygenated. The heart performs these mechanical pumping functions cyclically. Each cycle, known as the cardiac cycle, includes systole and diastole. Systole is the ejection phase of the cardiac cycle, during which the ventricles eject blood. Diastole is the relaxation phase of the cardiac cycle. Primary functions of diastole include filling the ventricles with blood for the next ejection (systolic) phase and allowing perfusion of the myocardial tissue. The filling of the LV includes a fast (active) filling phase followed by a slow (passive) filling phase. During the fast filling phase, the walls of LV spring back to their relaxation state after blood ejection, thereby drawing blood from the LA into the LV. During the slow filling phase, blood continues to be drawn into the LV by a pressure gradient between the LA and the LV.

In a normal heart, the sinus node, the heart's natural pacemaker, generates electrical signals, called action potentials, that propagate through an electrical conduction system to various regions of the heart to excite the myocardial tissues of these regions. Coordinated delays in the propagations of the action potentials in a normal electrical conduction system cause the various portions of the heart to contract in synchrony to result in efficient pumping functions. A blocked or otherwise abnormal electrical conduction and/or deteriorated myocardial tissue cause dysynchronous contraction and relaxation of the heart, resulting in poor hemodynamic performance, including a diminished blood supply to the heart and the rest of the body. The abnormal electrical conduction and/or deteriorated myocardium result in systolic dysfunction—because the myocytes do not contract in unison—and diastolic dysfunction—because the myocytes do not relax in unison. The relative degree of diastolic and systolic impairment will vary during different stages of the disease. Decreased systolic and diastolic performance each contribute to overall hemodynamic performance.

For these and other reasons, there is a need for providing an effective treatment for the diastolic dysfunction.

SUMMARY

Pacing pulses are delivered to one or more cardiac regions to improve diastolic performance in patients having diastolic dysfunction and/or heart failure. A cardiac pacing system executes a pacing algorithm using a parameter indicative of the diastolic performance as an input. The pacing pulses excite the one or more cardiac regions to redistribute the loading on the ventricular wall during diastole, thereby improving the diastolic performance by lowering the degree of cardiac wall motion dyssynchrony associated with diastolic dysfunction.

In one embodiment, a cardiac pacing system includes a sensing circuit, a pacing circuit, a diastolic performance sensor, a signal processor, and a pacing controller. The sensing circuit senses one or more cardiac signals. The pacing circuit delivers pacing pulses. The diastolic performance sensor senses a signal indicative of a diastolic function. The signal processor receives and processes the signal indicative of the diastolic function, and includes a diastolic performance parameter generator that produces a diastolic performance parameter based on the signal indicative of the diastolic function. The pacing controller receives the diastolic performance parameter and controls the delivery of the pacing pulses based on the one or more cardiac signals and the diastolic performance parameter.

In one embodiment, a cardiac rhythm management system includes an implantable pacemaker and one or more implantable intracardiac leads. The implantable pacemaker includes a sensing circuit, a pacing circuit, a diastolic performance sensor, and a pacing algorithm execution module. The sensing circuit senses one or more cardiac signals. The pacing circuit delivers pacing pulses. The diastolic performance sensor senses a signal indicative of a diastolic function. The pacing algorithm execution module controls the delivery of the pacing pulses based on a predetermined pacing algorithm, the one or more cardiac signals, and the signal indicative of the diastolic function. The one or more implantable intracardiac leads provide electrical connections between the implantable pacemaker and a heart.

In one embodiment, a method for improving diastolic performance uses cardiac pacing. One or more cardiac signals and a signal indicative of a diastolic function are sensed. A diastolic performance parameter is derived from the signal indicative of the diastolic function. A predetermined cardiac pacing algorithm is executed using at least the diastolic performance parameter as an input. According to the pacing algorithm, pacing pulses are delivered to the heart.

In one embodiment, cardiac pacing is determined and delivered to improve diastolic performance. The effectiveness of delivering pacing pulses to improve a measure of diastolic performance is predicted. After the effectiveness is predicted, the pacing pulses are delivered to one or more cardiac regions to improve the diastolic performance.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

BRIEF DESCRIPTION OF THE DRAWINGS

The drawings, which are not necessarily drawn to scale, illustrate generally, by way of example, but not by way of limitation, various embodiments discussed in the present document.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

This document discusses, among other things, a cardiac pacing method and apparatus for improving diastolic performance in patients suffering diastolic dysfunction and/or heart failure. Such patients generally have an ejection fraction of greater than 50%, an absence of significant mitral regurgitation, and symptoms of heart failure resulted from problems in the relaxation of the heart.

Left ventricular (LV) mechanical dyssynchrony (also referred to as asynchrony) due to delayed electrical activation has been shown to impact LV systolic function. Cardiac resynchronization therapy (CRT) improves hemodynamic performance by delivering pacing pulses to one or more regions in lateral ventricular walls such that the ventricles contract in synchrony to result in a more efficient ejection of blood during systole. A study indicates that most patients with diastolic dysfunction also have significant LV dyssynchrony, with abnormally heavy loading on the septal wall. Thus, a treatment for these patient includes delivering pacing pulses to pre-excite the septal wall, thereby reducing the loading on the septal wall and providing a more uniform distribution of loading across the LV wall. More generally, pacing pulses are delivered to one or more most heavily loaded cardiac regions, i.e., the regions that contribute the most to the contraction or the ejection of blood, to restore LV mechanical synchrony during diastole.

Figure 1A:
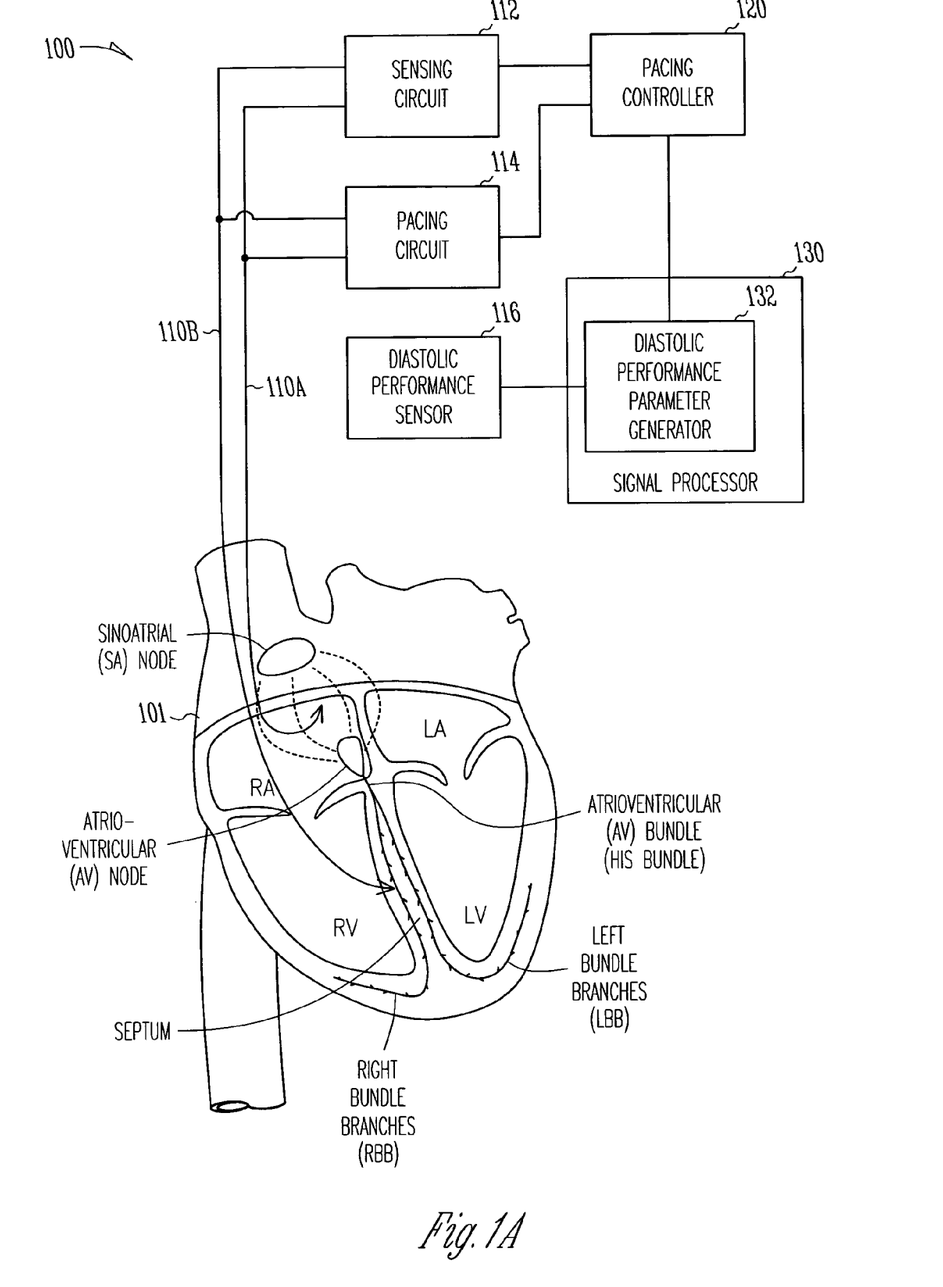
FIG. 1A is a schematic/block diagram illustrating one embodiment of a cardiac pacing system for treating the diastolic dysfunction and portions of an environment in which the system is used.

FIG. 1A is a schematic/block diagram illustrating one embodiment of a cardiac pacing system 100 for improving diastolic performance and portions of the environment in which system 100 is used. In one embodiment, cardiac pacing system 100 includes leads 110A-B, a sensing circuit 112, a pacing circuit 114, a diastolic performance sensor 116, a signal processor 130, and a pacing controller 120.

Leads 110A-B are intracardiac pacing leads each including one or more electrodes for sensing electrogram from and delivering pacing pulses to a predetermined region within a heart 101. Leads 110A-B provide for electrical connections between sensing circuit 112 and heart 101 and between pacing circuit 114 and heart 101. In one embodiment, diastolic performance sensor 116 is also incorporated into one of leads 110A-B for intracardiac placement. In the embodiment illustrated in FIG. 1, lead 110A is an atrial pacing lead with one or more electrodes for placement in the RA of heart 101, lead 110B is an transeptal pacing lead with at least one electrode fixable onto the septum of heart 101. One example of the transeptal pacing lead providing for access to the septum through the RV for LV septal excitation by pacing is discussed in U.S. Pat. No. 5,728,140, "METHOD FOR EVOKING CAPTURE OF LEFT VENTRICLE USING TRANSEPTAL PACING LEAD," assigned to Cardiac Pacemakers, Inc., which is hereby incorporated by reference in its entirety. In other embodiments, cardiac pacing system 100 includes one or more pacing leads in additional to leads 110A-B to provide access to additional intracardiac regions, such as regions within the RV and/or LV including additional septal regions.

In the embodiment illustrated in FIG. 1A, sensing circuit 112 senses RA and septal electrograms through leads 110A-B, and pacing circuit 114 delivers pacing pulses to at least the septum through lead 10B. In one embodiment, pacing circuit 114 delivers pacing pulses to RA and the septum through leads 110A-B. In other embodiments, where additional leads are included, sensing circuit 112 senses additional electrograms and, when necessary, pacing circuit 114 delivers pacing pulses to additional sites through the additional leads.

Pacing controller 120 controls whether, where, and when to deliver the pacing pulses using the electrograms and a diastolic performance parameter as inputs. Diastolic performance sensor 116 senses a signal indicative of a diastolic function. Signal processor 130 process the signal. In one embodiment, signal processor 130 includes a diastolic performance parameter generator 132 to produce the diastolic performance parameter based on the signal indicative of the diastolic function.

In one embodiment, diastolic performance sensor 116 includes a pressure sensor to sense a signal indicative of an LV pressure. In one specific embodiment, diastolic performance sensor 116 is placed in the LV to directly sense the LV pressure. In other embodiments, diastolic performance sensor 116 indirectly senses the LV pressure, by sensing another pressure having a known or predictable relationship with the LV pressure. Examples of pressures having known or predictable relationships with the LV pressure during all or a portion of the cardiac cycle include an LA pressure and a coronary vein pressure. One specific example of measuring the LV pressure using a coronary vein pressure sensor is discussed in U.S. patent application Ser. No. 10/038,936, "METHOD AND APPARATUS FOR MEASURING LEFT VENTRICULAR PRESSURE," filed on Jan. 4, 2002, assigned to Cardiac Pacemakers, Inc., which is hereby incorporated by reference in its entirety. In one embodiment, diastolic performance parameter generator 132 includes a diastolic pressure detector to detect a left ventricular end diastolic pressure (LVEDP) from the signal indicative of the LV pressure. The diastolic performance parameter is the LVEDP. In another embodiment, diastolic performance parameter generator 132 includes a diastolic pressure timer to measure a time constant (tau) related to a decrease in the left ventricular pressure. The diastolic performance parameter is that time constant.

In another embodiment, diastolic performance sensor 116 includes a pulmonary flow sensor to sense a signal indicative of a pulmonary venous blood flow. In one specific embodiment, the pulmonary flow sensor includes a pulmonary impedance sensing circuit to sense the pulmonary impedance, indicative of the pulmonary blood volume. Diastolic performance parameter generator 132 includes a velocity detector to calculate an antegrade pulmonary venous blood velocity based on the signal indicative of the pulmonary venous blood flow. The diastolic performance parameter is the pulmonary venous blood velocity.

In another embodiment, diastolic performance sensor 116 includes a mitral flow sensor to sense a signal indicative of blood flow through the mitral valve. In one specific embodiment, the mitral flow sensor includes an impedance sensor to a measure an LV volume. The LV volume is derived from an impedance measured between electrodes in the right ventricle and in a left ventricular coronary vein. One example of such an impedance sensor and measurement is discussed in U.S. Pat. No. 6,278,894, "MULTI-SITE IMPEDANCE SENSOR USING CORONARY SINUS/VEIN ELECTRODES," assigned to Cardiac Pacemakers, Inc., which is hereby incorporated by reference in its entirety. The time-derivative of this LV volume signal during diastole (after the opening of the mitral valve at the end of ejection) is a measure of the blood flow through the mitral valve. The peak blood flow during diastole, the duration of the rapid initial blood flow during diastole, and the time constant of the decrease in the blood flow during diastole are all useful measures of diastolic performance. Diastolic performance parameter generator 132 includes one or more of a peak detector to detect the peak blood flow, a timer to measure the duration of the rapid initial blood flow, and another timer to measure the time constant of the decrease in the blood flow. The diastolic performance parameter includes one of the peak blood flow, the duration of the rapid initial blood flow, and the time constant of the decrease in the blood flow during diastole.

In another embodiment, diastolic performance sensor 116 includes an acoustic sensor to sense a signal indicative of heart sounds. In one specific embodiment, the acoustic sensor includes an accelerometer. In another specific embodiment, the acoustic sensor includes a microphone. Diastolic performance parameter generator 132 includes a heart sound analyzer to detect a diastolic acoustic noise from the signal indicative of heart sounds. The diastolic performance parameter is the diastolic acoustic noise. The diastolic acoustic noise is the total acoustic noise measured over the diastolic phase of one cardiac cycles. Examples of methods for calculating the total acoustic noise measured over a predetermined time period are discussed in U.S. Pat. No. 6,044,298, "OPTIMIZATION OF PACING PARAMETERS BASED ON MEASUREMENT OF INTEGRATED ACOUSTIC NOISE," and U.S. Pat. No. 6,058,329, "OPTIMIZATION OF PACING PARAMETERS BASED ON MEASUREMENT OF ACOUSTIC NOISE," both assigned to Cardiac Pacemakers, Inc., which are hereby incorporated by reference in their entirety.

Figure 1B:
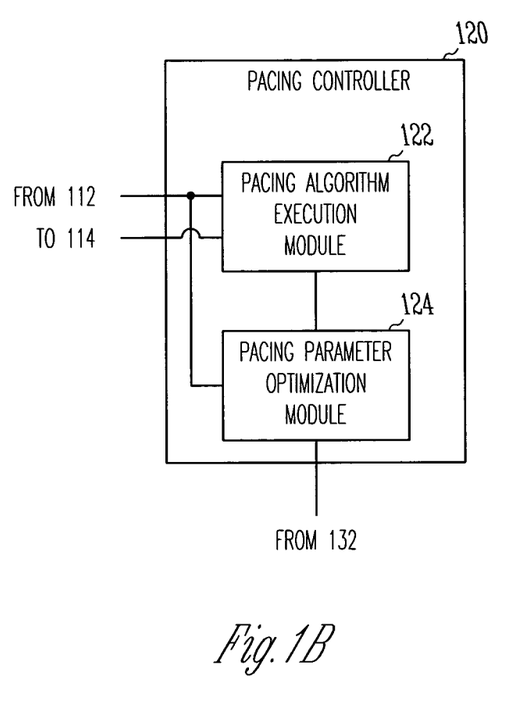
FIG. 1B is a schematic/block diagram illustrating one embodiment of a pacing controller of the cardiac pacing system of FIG. 1A.

FIG. 1B is a schematic/block diagram illustrating one embodiment of pacing controller 120. Pacing controller 120 receives the diastolic performance parameter and uses it to determine and/or adjust one or more pacing parameters. Pacing controller 120 includes a pacing parameter optimization module 124 and a pacing algorithm execution module 122. Pacing parameter optimization module 124 receives the diastolic performance parameter and calculates one or more approximately optimal pacing parameters based on at least the diastolic performance parameter. In one embodiment, the approximately optimal pacing parameter is a pacing parameter predicted to provide a target value (including a maximum or minimum value) for the diastolic performance parameter. In another embodiment, the approximately optimal pacing parameter is a pacing parameter predicted to maintain a threshold value for the diastolic performance parameter. In one specific embodiment, the target or threshold value for the diastolic performance parameter is determined based on systemic considerations including both systolic and diastolic performance of heart 101. In one embodiment, pacing parameter optimization module 124 includes a pacing site selector to select one or more pacing sites and a pacing timing calculator to calculate one or more pacing timing parameters such as atrioventricular and interventricular pacing delays. Pacing algorithm execution module 122 controls the delivery of the pacing pulses by executing a predetermined pacing algorithm using the one or more approximately optimal pacing parameters. In one embodiment, the predetermined pacing algorithm defines an atrial tracking pacing mode such as a DDD or a VDD mode. The one or more approximately optimal pacing parameters include an atrioventricular pacing delay. In one embodiment, wherein multiple ventricular leads are applied to provide sensing and pacing of multiple ventricular sites, the one or more approximately optimal pacing parameters include one or more atrioventricular pacing delays, one or more interventricular pacing delays, and/or one or more pacing sites to which pacing pulses are actually delivered.

Figure 2:
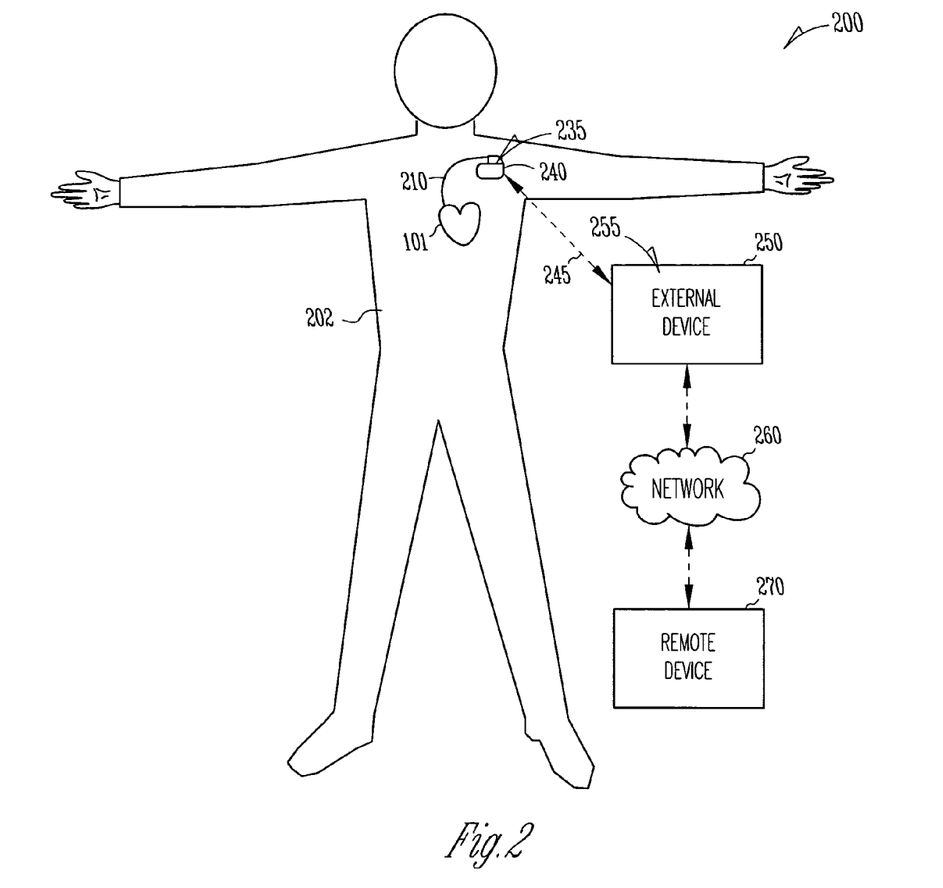
FIG. 2 is a schematic/block diagram illustrating one embodiment of portions a cardiac rhythm management (CRM) system including the cardiac pacing system of FIG. 1A and portions of an environment in which the CRM system is used.

FIG. 2 is a schematic/block diagram illustrating one embodiment of portions of a cardiac rhythm management (CRM) system 200 and portions of the environment in which system 200 is used. CRM system 200 incorporates cardiac pacing system 100 to provide a pacing therapy to heart 101. In one embodiment, CRM system 200 includes an implantable system 235, an external system 255, and a telemetry link 245 providing for bidirectional communication between implantable system 235 and external system 255. Implantable system 235 includes an implantable device 240 and a lead system 210. Implantable device 240 is implanted within a body 202 and coupled to heart 101 via lead system 210. Examples of implantable device 240 include pacemakers, pacemaker/defibrillators, cardiac resynchronization devices, cardiac remodeling control devices, and any other implantable medical devices with a pacing function. In one embodiment, lead system 210 includes leads 110A-B and additional pacing leads, if any. In another embodiment, diastolic performance sensor 116 is incorporated in a lead of lead system 210. In one embodiment, external system 255 is a patient management system including an external device 250 in proximity of implantable device 240, a remote device 270 in a relatively distant location, and a telecommunication network 260 linking external device 250 and remote device 270. An example of such a patient management system is discussed in U.S. patent application Ser. No. 10/323,604, "ADVANCED PATIENT MANAGEMENT FOR DEFINING, IDENTIFYING AND USING PREDETERMINED HEALTH-RELATED EVENTS," filed on Dec. 18, 2002, assigned to Cardiac Pacemakers, Inc., which is incorporated herein by reference in its entirety. The patient management system allows access to implantable system 235 from a remote location, for purposes such as monitoring patient status and adjusting therapies. In another embodiment, external system 255 includes a programmer. In one embodiment, telemetry link 245 is an inductive telemetry link. In an alternative embodiment, telemetry link 245 is a far-field radio-frequency telemetry link. In one embodiment, telemetry link 245 provides for data transmission from implantable device 240 to external system 255. This may include, for example, transmitting real-time physiological data acquired by implantable device 240, extracting physiological data acquired by and stored in implantable device 240, extracting therapy history data stored in implantable device 240, and extracting data indicating an operational status of implantable device 240 (e.g., battery status and lead impedance). In a further embodiment, telemetry link 245 provides for data transmission from external system 255 to implantable device 240. This may include, for example, programming implantable device 240 to acquire physiological data, programming implantable device 240 to perform at least one self-diagnostic test (such as for a device operational status), and programming implantable device 240 to deliver at least one therapy.

The physical distribution of cardiac pacing system 100 in CRM system 200 depends on practical factors such as the size and power constraints for an implantable device, computational power of the implantable device, and convenience of implementation and use. In one embodiment, cardiac pacing system 100 is included in implantable system 235. This embodiment allows for a diastolic performance based feedback loop (including diastolic performance sensor 116, signal processor 130, pacing controller 120, and pacing circuit 114) to operate continuously, without the need to communicate with external system 255. In another embodiment, portions of cardiac pacing system 100 are included in implantable system 235, and the remaining portions are included in external system 255. In one specific embodiment, external system 255 includes diastolic performance parameter generator 132 and pacing parameter optimization module 124. The signal sensed by diastolic performance sensor 116 is transmitted to external system 255 via telemetry link 245. One or more approximately optimal pacing parameters are transmitted to implantable device 240 via telemetry 245. Including portions of cardiac pacing system 100 in external system reduces size, power, and/or computational demands on implantable device 240.

Figure 3:
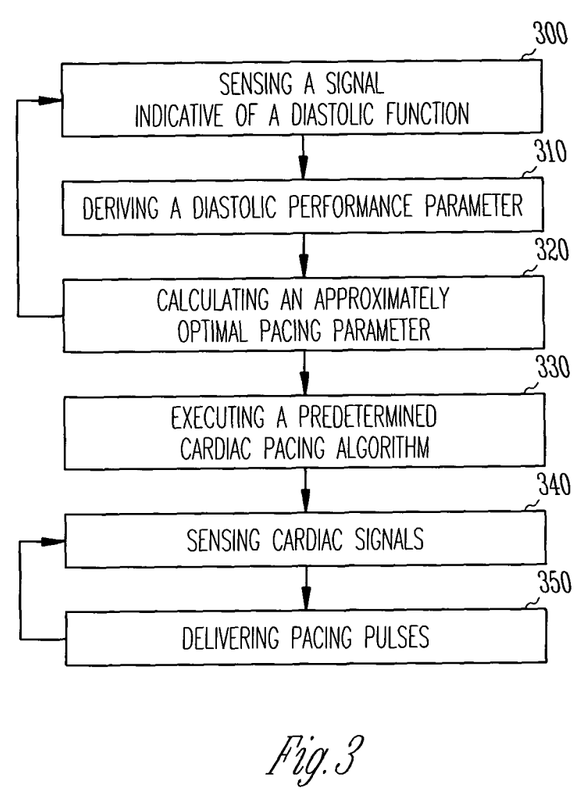
FIG. 3 is a flow chart illustrating one embodiment of a method for improving diastolic performance by cardiac pacing.

FIG. 3 is a flow chart illustrating one embodiment of a method for improving diastolic performance by cardiac pacing. The method determines and adjusts one or more pacing parameters based on a sensed signal indicative of a diastolic function. In one embodiment, the method is performed by cardiac pacing system 100.

The signal indicative of the diastolic function is sensed at 300. A diastolic performance parameter is derived from that signal at 310. In one embodiment, the signal indicative of the diastolic function is a signal indicative of an LV pressure, and the diastolic performance parameter is an LVEDP measured from the signal indicative of the LV pressure. In another embodiment, the signal indicative of the diastolic function is a signal indicative of an LV pressure, and the diastolic performance parameter is a time constant (tau) related to a decrease in the LV pressure. In another embodiment, the signal indicative of the diastolic function is a signal indicative of a pulmonary venous blood flow, and the diastolic performance parameter is an antegrade pulmonary venous blood velocity calculated based on the signal indicative of the pulmonary venous blood flow. In another embodiment, the signal indicative of the diastolic function is a signal indicative of blood flow through the mitral valve, and the diastolic performance parameter is the peak blood flow, the duration of the initial blood flow peak, or time constant related to the decrease in the blood flow during diastole. In another embodiment, the signal indicative of the diastolic function is a signal indicative of heart sounds, and the diastolic performance parameter is a diastolic acoustic noise detected from the signal indicative of heart sounds.

One or more approximately optimal pacing parameters are calculated based on at least the diastolic performance parameter at 320. In one embodiment, the one or more approximately optimal pacing parameters include one or more pacing timing parameters such as atrioventricular pacing delays and interventricular pacing delays. In another embodiment, the one or more approximately optimal pacing parameters include one or more pacing sites. The one or more pacing sites includes one or more ventricular regions doing most of the work in ventricular contraction and blood ejection. In one embodiment, the one or more pacing sites includes at least one site in the ventricular septum. In one specific embodiment, the one or more pacing sites includes at least one site in the LV septum.

A predetermined pacing algorithm is executed at 330. The pacing algorithm execution includes generating commands to control a delivery of pacing pulses. As the predetermined pacing algorithm is being executed, cardiac signals are sensed at 340, and pacing pulses are delivered at 350. The pacing algorithm applies a set of predetermined pacing logic rules and parameters to determine the timing and/or site for each pacing pulse delivery using the one or more approximately optimal pacing parameters and the sensed cardiac signals as inputs.

Figure 4:
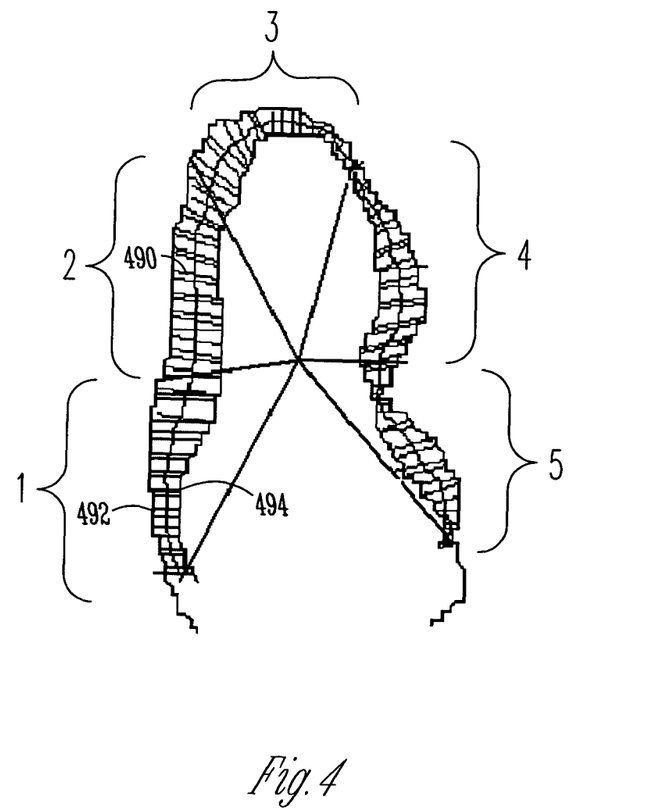
FIG. 4 is an exemplary LV regional displacement diagram used for determining sites for placement of one or more ventricular pacing electrodes.

FIG. 4 is an exemplary LV regional displacement diagram used for determining sites for placement of one or more ventricular pacing electrodes. To deliver the pacing pulses to improve diastolic performance, implantable device 240 and lead system 210 are implanted in body 202. The implantation of lead system 210 includes placement of electrodes on each lead in predetermined cardiac sites.

In one embodiment, an LV echocardiogram is recorded and analyzed using an echocardiographic analysis system such as Echo-CMS (Echocardiographic Measurement System) by Medis, Leiden, Netherlands (Medis Echo-CMS). The Medis Echo-CMS automatically detects LV wall motion contours in sequential echocardiographic image frames over several (e.g., two to five) cardiac cycles, and calculates average LV regional endocardial displacement over one cardiac cycle for 100 equally spaced segments on the LV wall motion contours, as illustrated in FIG. 4. An example of such an embodiment is discussed in U.S. patent application Ser. No. 10/402,324, "METHOD AND APPARATUS FOR QUANTIFICATION OF CARDIAC WALL MOTION ASYNCHRONY," filed on Mar. 28, 2003, assigned to Cardiac Pacemakers, Inc., which is incorporated herein by reference in its entirety.

In FIG. 4, the magnitudes of the LV regional endocardial displacement are shown by lines 490 for the 100 equally spaced segments on the LV wall motion contours. Contours 492 and 494 show the overall LV endocardial displacement range over one cardiac cycle. The distance between contours 492 and 494 at any region shows the wall displacement over one cardiac cycle for that region. As illustrated in FIG. 4, twenty contiguous segments of the 100 equally spaced segments on the LV wall motion contours are combined into five regions labeled 1 through 5. The LV septal wall is on the left and approximately includes regions 1 and 2. In one embodiment, diastolic performance is improved by delivering pacing pulses to pre-excite the region showing the largest LV regional displacement covariant with the overall LV area or volume change, i.e., the region contributing the most to LV contraction or ejection of the blood from the LV. In the example of FIG. 4, pacing pulses are to be delivered to at least region 2.

Figure 5:
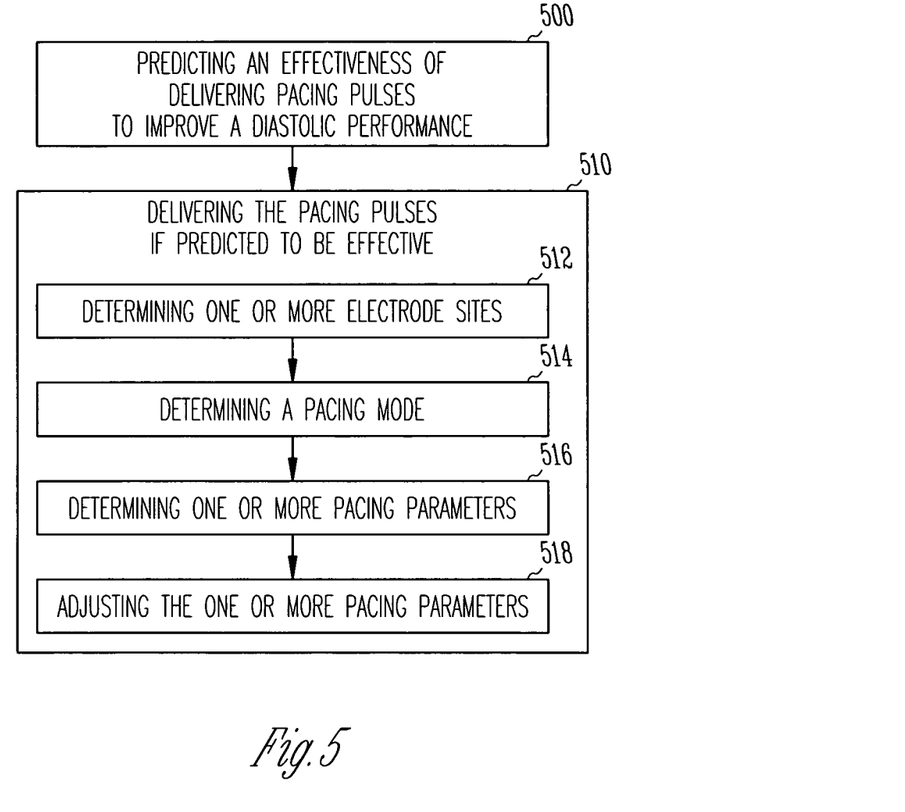
FIG. 5 is a flow chart illustrating one embodiment of a procedure for determining and delivering a pacing therapy to improve diastolic performance.

FIG. 5 is a flow chart illustrating one embodiment of a procedure for determining and delivering a pacing therapy to improve diastolic performance. The effectiveness of delivering pacing pulses to improve a measure of diastolic performance is being predicted at 500. The effectiveness is predicted when a patient is diagnosed to have conditions meeting a set of criteria and accepts the therapy. The criteria include, by way of example, but not by way of limitation, an ejection fraction greater than 50%, absence of significant mitral regurgitation, and manifestation of symptoms of heart failure due to high filling LA pressures. In one embodiment, the effectiveness prediction further includes an echocardiographic analysis providing an LV regional displacement diagram such as the one shown in FIG. 4. The effectiveness of delivering pacing pulses to improve the diastolic performance is predicted when the LV regional endocardial displacements are significantly non-uniform across the LV wall. In one embodiment, the LV endocardial wall is divided into multiple regions. An average LV regional endocardial displacement is calculated for each of the regions. In one specific embodiment, the effectiveness of delivering pacing pulses is predicted when the average LV regional endocardial displacement of at least one of the regions exceeds a predetermined threshold. In another specific embodiment, the effectiveness of delivering pacing pulses is predicted or when the largest difference between the average LV regional endocardial displacements for any two of the regions exceeds a predetermined threshold.

If delivering pacing pulses is predicted to be effective and accepted by the patient, the pacing pulses are delivered to one or more cardiac regions to treat the diastolic dysfunction at 510. Delivering the pacing pulses includes determining one or more electrode sites at 512, determining a pacing mode at 514, determining one or more pacing parameters at 516, and adjusting the one or more pacing parameters at 518.

In one embodiment, one or more ventricular regions showing the most contribution to the LV contraction are selected as the one or more electrode sites at 512. An electrode site is the site for the placement of an electrode during lead implantation as discussed above with reference to FIG. 4. A study has shown that the one or more pacing sites likely include at least one site in an LV septal region. In one specific embodiment, the LV septal region is paced using an insulated electrode fixed into the septum through the right ventricle, as discussed above (U.S. Pat. No. 5,728,140). One specific example of a method for determining the one or more electrode sites is discussed above with reference to FIG. 4.

In one embodiment, an atrial tracking mode is selected at 514. If the patient retains a normal sinus rhythm, a VDD pacing mode is selected. Otherwise, a DDD pacing mode is selected. The VDD and DDD pacing modes each include a multi-ventricular-site version when more than one ventricular pacing sites are selected.

In one embodiment, one or more pacing parameters are determined based on a diastolic performance parameter at 516. This includes sensing a signal indicative of a diastolic function and deriving the one or more pacing parameters from the sensed signal. Specific examples of a method for determining one or more approximately optimal pacing parameters are discussed above with reference to FIG. 3. In one specific embodiment, after the one or more electrode sites are selected at 512, they are individually activated using a pacing parameter specifying one or more actual pacing sites. In one specific embodiment, the one or more actual pacing sites are determined by selecting from the one or more electrode sites on a beat-by-beat basis.

In one embodiment, after an initial determination, the one or more pacing parameters are adjusted at 518. This includes sensing the signal indicative of the diastolic function and updating the one or more pacing parameters based on the sensed signal. In one specific embodiment, the one or more pacing parameters are dynamically and continuously adjusted. In another specific embodiment, the one or more pacing parameters are periodically adjusted. In another specific embodiment, the one or more pacing parameters are adjusted when a need develops, such as when the patient's physiological or pathological condition changes.

In one embodiment, the pacing pulses are delivered to treat diastolic dysfunction as well as other pathological conditions such as systolic dysfunction. In one embodiment, steps 512, 514, 516, and 518 are each performed as part of a systemic approach optimizing a therapy for improving an overall hemodynamic performance. In one specific embodiment, the one or more pacing parameters are determined and adjusted to improve both systolic and diastolic performances. In one specific embodiment, the one or more pacing parameters are determined and adjusted to maintain predetermined minimum systolic and minimum diastolic performance. In another specific embodiment, the one or more pacing parameters are determined and adjusted to maintain a minimum systolic performance while maximizing the diastolic performance, or to maintain a minimum diastolic performance while maximizing the systolic performance. Examples of determining approximately optimal pacing parameters for improving systolic performance are discussed in U.S. patent application Ser. No. 10/314,910, "METHOD AND APPARATUS FOR OPTIMIZING VENTRICULAR SYNCHRONY DURING DDD RESYNCHRONIZATION THERAPY USING ADJUSTABLE ATRIO-VENTRICULAR DELAYS," and U.S. patent application Ser. No. 10/314,899, "METHOD AND APPARATUS FOR OPTIMIZING STROKE VOLUME DURING DDD RESYNCHRONIZATION THERAPY USING ADJUSTABLE ATRIO-VENTRICULAR DELAYS," both filed on Dec. 9, 2002, assigned to Cardiac Pacemakers, Inc., which are hereby incorporated by reference in their entirety.

It is to be understood that the above detailed description is intended to be illustrative, and not restrictive. Other embodiments, including any possible combinations of the elements of the apparatus and methods discussed in this document, will be apparent to those of skill in the art upon reading and understanding the above description. For example, the electrical therapy for diastolic dysfunction can be applied in conjunction with a chemical therapy and/or a biological therapy.

The scope of the invention should, therefore, be determined with reference to the appended claims, along with the full scope of equivalents to which such claims are entitled.

What is claimed is:

1. A method, comprising:
   predicting an effectiveness of delivering pacing pulses to improve a measure of diastolic performance, wherein predicting the effectiveness includes:
   recording a left ventricular echocardiogram;
   dividing a left ventricular endocardial wall into multiple regions;
   measuring left ventricular regional endocardial wall displacements over at least one cardiac cycle for each of the regions using the recorded left ventricular echocardiogram; and
   predicting the effectiveness if the left ventricular regional endocardial wall displacements are significantly non-uniform across the left ventricular endocardial wall; and
   delivering the pacing pulses to one or more cardiac regions to improve the diastolic performance in response to the effectiveness being predicted.

2. The method of claim 1, further comprising determining one or more electrode sites corresponding to the one or more cardiac regions.

3. The method of claim 2, wherein determining the one or more electrode sites comprises selecting one or more ventricular regions showing most contribution to a left ventricular contraction.

4. The method of claim 3, wherein determining the one or more electrode sites comprises identifying one or more regions displaying largest left ventricular regional endocardial wall displacements covariant with overall left ventricular area or volume changes.

5. The method of claim 1, wherein delivering the pacing pulses to the one or more cardiac regions comprises delivering the pacing pulses to excite one or more left ventricular septal regions.

6. The method of claim 5, further comprising introducing at least one insulated electrode into a septum through a right ventricle.

7. The method of claim 1, further comprising determining a pacing mode.

8. The method of claim 7, wherein delivering the pacing pulses comprising executing a pacing algorithm defining a VDD pacing mode.

9. The method of claim 7, wherein delivering the pacing pulses comprising executing a pacing algorithm defining a DDD pacing mode.

10. The method of claim 1, further comprising determining one or more pacing parameters, including sensing a signal indicative of a diastolic function and deriving the one or more pacing parameters from the sensed signal indicative of the diastolic function.

11. The method of claim 10, further comprising adjusting the one or more pacing parameters dynamically and continuously.

12. The method of claim 10, further comprising adjusting the one or more pacing parameters periodically.

13. The method of claim 10, further comprising adjusting the one or more pacing parameters in response to a change of a cardiac condition.

14. The method of claim 10, wherein determining the one or more pacing parameters comprises determining the one or more pacing parameters to improve at least a measure of systolic performance and a measure of diastolic performance.

* * * * *